US005852059A

United States Patent [19]
Thompson

[11] Patent Number: 5,852,059
[45] Date of Patent: Dec. 22, 1998

[54] USE OF DROLOXIFENE FOR THE TREATMENT OF PROTASTIC DISEASE, ENDOMETRIOSIS AND OBESITY

[75] Inventor: David D. Thompson, Gales Ferry, Conn.

[73] Assignee: Pfizer Inc., New York, N.Y.

[21] Appl. No.: 750,860

[22] PCT Filed: May 26, 1995

[86] PCT No.: PCT/IB95/00404

§ 371 Date: Jan. 6, 1997

§ 102(e) Date: Jan. 6, 1997

[87] PCT Pub. No.: WO96/02243

PCT Pub. Date: Feb. 1, 1996

Related U.S. Application Data

[63] Continuation-in-part of Ser. No. 276,969, Jul. 19, 1994, Pat. No. 5,441,986.

[51] Int. Cl.$^6$ ................................................ A61K 31/135
[52] U.S. Cl. ............................................................ 514/648
[58] Field of Search ............................................... 514/648

[56] References Cited

U.S. PATENT DOCUMENTS

| 5,047,431 | 9/1991 | Schickaneder et al. | 514/648 |
| 5,254,594 | 10/1993 | Niikura et al. | 514/648 |
| 5,384,332 | 1/1995 | Fontana | 514/648 |
| 5,426,123 | 6/1995 | Fontana | 514/648 |
| 5,455,275 | 10/1995 | Fontana | 514/648 |

OTHER PUBLICATIONS

Gill–Sharma, M.K., et al., "Effects of Tamoxifen on the Fertility of Male Rats", Journal of Reproduction and Fertility 99, 395–402 (1993).

Schneider, M. R. et al., "Effect of zindoxifene on experimental prostatic tumours of the rat", J Cancer Res Clin Oncol 117:33–36 (1991).

Faulkner, et al., "Regional and Total Body Bone Mineral Content, Bone Mineral Density, and Total Body Tissue Composition in Children 8–16 Years of Age" Calcified tissue 53:7–12 (1993).

Jones, Robert C., "The Effect of a Luteinizing Hormone Releasing Hormone (LRH) Agonist (Wy–40,972), Levonorgestrel, Danazol and Ovariectomy on Experimental Endometriosis in the Rat" Acta Endocrinologica 106, 282–8 (1984).

Wiseman, H., "Tamoxifen: New Membrane–Mediated Mechanisms of Action and Therapeutic Advances", Tips, 101–15 (1994).

Wiseman, H., et al., "Droloxifene (3–hydroxytamoxifen) has membrane antioxidant ability: potential relevance to its mechanism of therapeutic action in breast cancer", Cancer Letters, 66 61–68 (1992).

Steinberg, D., et al., "Beyond Cholesterol Modifications of Low–Density Lipoprotein that Increase its Atherogenicity", The New England Journal of Medicine, 915–924 (1989).

Wiseman, H., et al., Protective actions of tamoxifen and 4–hydroxytamoxifen against oxidative damage to human low–density lipoproteins: a mechanism accounting for the cardioprotective action of tamoxifen?, Biochem, J. 292 635 (1993).

Pritchard, K., "Summary", Am. J. Clin. Oncol., 14 (Suppl. 2) S62–S63 (1991).

Cypriani, B., "Role of Estrogen Receptors and Antiestrogen Binding Sites in an Eary Effect of Antiestrogens, the Inhibition of Cholestrol Biosynthesis", J. Steroid Biochem., vol. 31, No. 5, 763–771, (1988).

Bruning, P.F., "Droloxifene, A New Anti–estrogen in Postmenopausal Advanced Breast Cancer: Preliminary Results of a Double–blind Dose–finding Phase II Trial", Eur F Cancer, vol. 28A, No., 8/9, 1404–1407 (1992).

Neubauer, B. L., et al., "Endocrine and Antiprostatic Effects of Raloxifene (LY156758) in Male Rat", The Prostate, 23:245–262 (1993).

Wiseman, H., et al., "Tamoxifen Inhibits Lipid Peroxidation in Cardiac Microsomes", Biochemical Pharmacology, vol. 45, No. 9, 1851–1855 (1993).

Love, R. R., "Effects of Tamoxifen on Cardiovascular Risk Factor in Postmenopausal Women", Annals of Internal Medicine, 115, 860–864 (1991).

Schwartz, J. et al., "Clinical Pharmacology of Estrogens: Cardiovascular Actions and Cardioprotective Benefits of Replacement Therapy in Postmenopausal Women", J. Clin. Pharmacol, 35:314–329 (1995).

Bierman, E.L., "Atherosclerosis and other forms of arteriosclerosis", 1106–1110 (1989).

"Raloxifene Hydrochloride EN=090328", Drugs of the Future, vol. 15(7), 762–63 (1990).

*Primary Examiner*—Jerome D. Goldberg
*Attorney, Agent, or Firm*—Peter C. Richardson; Gregg C. Benson; Mervin E. Brokke

[57] ABSTRACT

This invention provides a method for treating a condition or disease selected from endometriosis, obesity, benign prostatic hypertrophy and prostatic carcinoma in mammals which comprises administering to said mammal an amount of droloxifene or a pharmaceutically acceptable salt thereof which is effective in treating said condition or disease.

2 Claims, No Drawings

USE OF DROLOXIFENE FOR THE TREATMENT OF PROTASTIC DISEASE, ENDOMETRIOSIS AND OBESITY

CROSS REFERENCE TO RELATED APPLICATIONS

This is a continuation-in-part of U.S. application Ser. No. 08/276,969 filed Jul. 19, 1994, now U.S. Pat. No. 5,441,986.

FIELD OF THE INVENTION

This invention relates to remedies for prostate diseases, endometriosis and obesity comprising, as active ingredient, droloxifene having the chemical structure represented by the following formula,

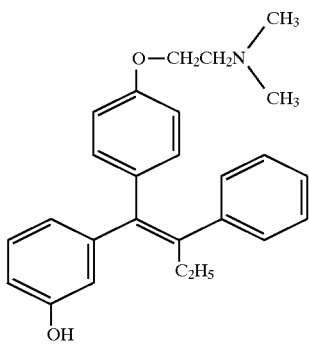

or a pharmaceutically acceptable salt thereof.

BACKGROUND OF THE INVENTION

Droloxifene is a known compound disclosed in U.S. Pat. No. 5,047,431 in which it is disclosed as an anti-tumor agent, particularly for treatment and prevention of cancer of the breast. Droloxifene is also useful for the relief of bone diseases caused by the deficiency of estrogen or the like, which are often observed in women after menopause or those with the ovaries removed. U.S. Pat. No. 5,254,594.

Gill-Sharma, et al., *J. Reproduction and Fertility* (1993) 99, 395, disclose that tamoxifen at 200 and 400 mg/kg/day reduces the weights of the testes and secondary sex organs in male rats.

Neubauer, et al., *The Prostate* 23: 245 (1993) teach that raloxifene treatment of male rats produced regression of the ventral prostate.

SUMMARY OF THE INVENTION

This invention provides a method for treating a condition or disease selected from endometriosis, obesity, benign prostatic hypertrophy and prostatic carcinoma in mammals which comprises administering to said mammal an amount of droloxifene or a pharmaceutically acceptable salt thereof which is effective in treating said condition or disease.

DETAILED DESCRIPTION OF THE INVENTION

The preparation of droloxifene (1-[4'-(2-dimethylaminoethoxy)phenyl]-1-(3'-hydroxyphenyl)-2-phenylbut-1-ene) and pharmaceutically acceptable salts thereof is described in U.S. Pat. No. 5,047,431 which is incorporated herein by reference.

As used in this application, "prostatic disease" means benign prostatic hyperplasia or prostatic carcinoma. "Treating" means curing, alleviating the symptoms of or preventing the onset of a disease or condition.

The remedies for the prostatic diseases, endometriosis and obesity of this invention comprise, as active ingredient, droloxifene or a salt thereof. The pharmaceutically acceptable salts of droloxifene are salts of non-toxic type commonly used, such as salts with organic acids (e.g., formic, acetic, citric, maleic, tartaric, methanesulfonic, benzenesulfonic or toluenesulfonic acids), inorganic acids (e.g. hydrochloric, hydrobromic, sulfuric or phosphoric acids), and amino acids (e.g., aspartic or glutamic acids). These salts may be prepared by the methods known to chemists of ordinary skill.

The remedies for the diseases and conditions of this invention may be administered to animals including humans orally or parenterally in the conventional form of preparations, such as capsules, microcapsules, tablets, granules, powder, troches, pills, suppositories, injections, suspensions and syrups.

The remedies for the diseases and conditions of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 1 mg to 100 mg in unit dosage for both oral and parenteral administration.

The active ingredient may be usually administered once to four times a day with a unit dosage of 0.25 mg to 100 mg in human patients, but the above dosage may be properly varied depending on the age, body weight and medical condition of the patient and the type of administration. One dose per day is preferred.

The following Examples will serve to illustrate, but do not limit the invention which is defined by the claims.

EXAMPLE 1

Effect on Prostate Weight

Male Sprague-Dawley rats, three months of age were administered by subcutaneous injection either vehicle (10% ethanol in water), estradiol (30 µg/kg), testosterone (1 mg/kg) or droloxifene citrate (10 mg/kg) daily for 14 days (n=6/group). After 14 days the animals were sacrificed, the prostate was removed and the wet prostate weight was determined. Mean weight was determined and statistical significance (p<0.05) was determined compared to the vehicle-treated group using Student's t-test.

Droxifene citrate at 10 mg/kg/day significantly (P<0.05) decreased prostate weight compared to vehicle. Testosterone had no effect while estrogen at 30 μg/kg significantly reduces prostate weight.

These data showed that droloxifene citrate is useful in the treatment of benign prostatic hypertrophy and prostatic cancer.

EXAMPLE 2

Effect on Body Fat Mass

Sprague-Dawley female rats at 10 months of age, weighing approximately 450 grams, were sham-operated (sham) or ovariectomized (OVX) and treated orally with vehicle, 17α ethynyl estradiol at 30 μg/kg/day or droloxifene citrate at 1.0, 2.5 or 5 mg/kg/day for 8 weeks. There were 6 to 7 rats in each sub group. On the last day of the study, body composition of all rats was determined using dual energy x-ray absorptiometry (Hologic QDR-1000/W) equipped with whole body scan software. See Faulkner, et al., *Calcified Tissue* 53, 7 (1993). Our results showed that ethynyl estradiol and all doses of droloxifene had no effect on lean body mass (in grams). However, the fat body mass (in grams) significantly decreased (40–60%) in OVX rats treated with ethynyl estradiol or droloxifene (at all dose levels) compared to sham or OVX controls. These results demonstrated that droloxifene is a useful agent in treatment of obesity.

EXAMPLE 3

Control and Prevention of Endometriosis

The protocol for surgically inducing endometriosis is identical to that described by Jones, *Acta Endocrinol* (Copenh) 106: 282–8. Adult Charles River Sprague-Dawley CD® female rats (200–240 g) are used. An oblique ventral incision is made through the skin and musculature of the body wall. A segment of the right uterine horn is excised, the myometrium is separated from the endometrium, and the segment is cut longitudinally. A 5×5 mm section of the endometrium, with the epithelial lining apposed to the body wall, is sutured at its four corners to the muscle using polyester braid (Ethiflex, 7-0®). The criterion of a viable graft is the accumulation of fluid similar to that which occurs in the uterus as a result of oestrogen stimulation.

Three weeks after transplantation of the endometrial tissue (+3 weeks) the animals are laparotomized, the volume of the explant (length×width×height) in mm was measured with calipers, and treatment is begun. The animals are injected so for 3 weeks with 10 to 1000 μg/kg/day of a compound of Formula I. Animals bearing endometrial explants are injected so with 0.1 ml/day of corn oil for 3 weeks served as controls. At the end of 3 week treatment period (+6 weeks), the animals are laparotomized and the volume of the explant determined. Eight weeks after cessation of treatment (+14 weeks) the animals are sacrificed; the explant are measured again.

Statistical analysis of the explant volume is by an analysis of variance.

EXAMPLE 4

| Droloxifene Citrate Tablets | |
|---|---|
| Droloxifene citrate | 100 g |
| Lactose | 1190 g |
| Low substituted hydroxypropylcellulose | 250 g |
| Polyvinylpyrrolidone | 50 g |
| Magnesium stearate | 10 g |

The components listed above are mixed together by the usual method, and the mixture thus obtained is compressed into 10,000 tablets each containing 10 mg of droloxifene citrate.

I claim:

1. A method of treating (a disease or condition selected from endometriosis,) prostatic carcinoma (and obesity) in mammals which comprises administering to a mammal in need of such treatment an amount of droloxifene or a pharmaceutically acceptable salt thereof which is effective in treating said (disease or condition) prostatic carcinoma.

2. A method of claim 1 wherein said pharmaceutically acceptable salt is the citrate salt.

* * * * *